US005510476A

United States Patent [19]
Ravikumar et al.

[11] Patent Number: 5,510,476
[45] Date of Patent: Apr. 23, 1996

[54] CARBOCATION SCAVENGING DURING OLIGONUCLEOTIDE SYNTHESIS

[75] Inventors: Vasulinga Ravikumar; Mark Andrade, both of Carlsbad, Calif.; Dennis Mulvey, Conroe, Tex.; Douglas L. Cole, San Diego, Calif.

[73] Assignee: Isis Pharmaceuticals, Inc., Carlsbad, Calif.

[21] Appl. No.: 271,181

[22] Filed: Jul. 7, 1994

[51] Int. Cl.$^6$ .......................... C07H 1/00; C07H 21/00; C07H 21/04; C07H 21/02
[52] U.S. Cl. .................. 536/25.31; 536/25.3; 536/25.33; 536/25.34
[58] Field of Search .................. 536/25.3, 25.31, 536/25.33, 25.34

[56] References Cited

U.S. PATENT DOCUMENTS

| | | | |
|---|---|---|---|
| Re. 34,069 | 9/1992 | Köster et al. | 536/25.3 |
| 4,415,732 | 11/1983 | Caruthers et al. | 536/26.5 |
| 4,458,066 | 7/1984 | Caruthers et al. | 536/25.34 |
| 4,500,707 | 2/1985 | Caruthers et al. | 536/25.34 |
| 4,517,338 | 5/1985 | Urdea et al. | 525/54.1 |
| 4,668,777 | 5/1987 | Caruthers et al. | 536/26.5 |
| 4,673,562 | 6/1987 | Davison et al. | 424/1.165 |
| 4,725,677 | 2/1988 | Köster et al. | 536/25.34 |
| 4,816,571 | 3/1989 | Andrus et al. | 536/25.3 |
| 4,973,679 | 11/1990 | Caruthers et al. | 536/26.71 |
| 5,132,418 | 7/1992 | Caruthers et al. | 536/25.3 |
| 5,210,264 | 5/1993 | Yau | 558/167 |

OTHER PUBLICATIONS

Alul et al., "Oxalyl–CPG: A Liable Support for Synthesis of Sensitive Oligonucleotide Derivatives", Nucleic Acids Research 19 : 1527–1532 (1991).

Beaucage et al., "Advances in the Synthesis of Oligonucleotides by the Phosphoramidite Approach", Tetra. Ltrs. 48:2223–2311 (1992).

Berner et al., "Studies on the Role of Tetrazole in the Activation of Phosphoramidites", Nuc. Acid. Res. 17: 853–864 (1989).

Bielinska et al., "Regulation of Gene Expression with Double–Stranded Phosphorothioate Oligonucleotides", Science 250: 997–1000 (1990).

Brenner et al., "Synthesis and Characterization of a Series of Isomeric Oxotechnetium (V) Diamido Dithiolates", Inorg. Chem. 23:3793–3797 (1984).

Brill et al., "Synthesis of Deoxydinucleoside Phosphorodithioates", J. Am. Chem. Soc. 113: 3972–3980 (1991).

Brill et al., "Synthesis of Oligodeoxynucleoside Phosphorodithioates via Thioamidites", J. Am. chem. Soc. 111: 2321–2322 (1989).

Dahl et al., "Mechanistic studies on the phosphoramidite coupling reaction in oligonucleotide synthesis. I. Evidence for nucleophilic catalysis by tetrazole and rate variations with the phosphorus substituents", Nucleic Acids Research 15:1729–1743 (1987).

Dahl, O., "Preparation of Nucleoside Phosphorothioates, Phosphorodithioates and Related Compounds" Sulfur Reports 11: 167–192 (1991).

Eckstein, F., "Nucleoside Phosphorothioates", Ann. Rev. Biochem. 54:367–402 (1985).

Kemp, D. S. et al., "Practical Preparation and Deblocking Conditions for N–α–(2–(p–biphenylyl)–2–propyloxycarbonyl)–amino acid (N–a–Bpoc–Xxx–OH) Derivatives" Int. J. Peptide Protein Res. 31, 359–372 (1988).

Kresse J. et al., "The Use of S–2–cyanoethyl Phosphorothioate in the Preparation of Oligo 5'–Deoxy–5'–Thiothymidylates" Nucleic Acids Research 2: 1–9 (1975).

Mehta et al., "Improved Efficiency and Selectivity in Peptide Synthesis: Use of Triethylsilane as a Carbocation Seavenger in Deprotection of t–Butyl Esters and t–Butoxycarbonyl––Protected Sites", Tetra.Ltrs. 33:5441–5444 (1992).

Nielson, J. et al., "Thermal Instability of Some Alkyl Phosphorodiamidites" J. Chem. Research (S) 26–27 (1986).

Pless, R. C. and Letsinger, R. L., "Solid Support of Oligothymidylates Using Phosphorochloridates and 1–alkylimidazoles" Nucleic Acids Research 2: 773–786 (1975).

Sekine et al., "Synthesis and Properties of S,S–Diaryl Nucleoside Phosphorodithioates in Oligonucleotide Synthesis" J. Org. Chem. 44: 2325–2326 (1979).

Wright et al., "Large Scale Synthesis of Oligonucleotides Via Phosphoramidite Nucleosides and a High–loaded Polystyrene Support" Tetrahedron Letters 34: 3373–3376 (1993).

Wu, H. et al., "Inhibition of in Vitro Transcription by Specific Double–Stranded Oligodeoxyribonucleotides" Gene 89: 203–209 (1990).

Yau, E. K., et al., "Synthesis of Dinucleoside and Dinucleotide Phosphorodithioates Via A Phosphotriester Approach" Tetrahedron Letters 31: 1953–1956 (1990).

Current Protocols In Molecular Biology, F. M. Ausubel, et al., Eds., Current Publications, 1993.

Green and Wuts, Protective Groups in Organic Synthesis, 2d edition, John Wiley & Sons, New York, 1991.

Sambrook, et al., Eds., Molecular Cloning, A Laboratory Manual Cold Spring Harbor Laboratory Press, 1989.

Maskos et al. Nucl. Acids Res. 20(7):1679–1684, 1992.

Pearson et al. Tetrahedron Letters 30:2739–2742, 1989.

*Primary Examiner*—Gary L. Kunz
*Attorney, Agent, or Firm*—Woodcock Washburn Kurtz Mackiewicz & Norris

[57] ABSTRACT

During the synthesis of oligonucleotides and phosphate linked oligomers, a carbocation scavenging agent is employed to increase the overall yield. The carbocation scavenging agent is used in conjunction with an acidic solution employed during the deprotection step.

24 Claims, No Drawings

CARBOCATION SCAVENGING DURING OLIGONUCLEOTIDE SYNTHESIS

FIELD OF THE INVENTION

This invention is directed to an improved process for synthesis of oligonucleotides and other phosphate linked oligomers. The invention includes the use of carbocation scavengers during the deblocking procedures of the oligomer synthesis. The process is useful for neutralizing carbocations formed during deblocking thereby increasing the overall efficiency of synthesis. The oligonucleotides and phosphate linked oligomers, in turn, are useful for diagnostic reagents, research reagents and in therapeutics.

BACKGROUND OF THE INVENTION

It is well known that most of the bodily states in multicellular organisms, including most disease states, are effected by proteins. Such proteins, either acting directly or through their enzymatic or other functions, contribute in major proportion to many diseases and regulatory functions in animals and man. For disease states, classical therapeutics has generally focused upon interactions with such proteins in efforts to moderate their disease-causing or disease-potentiating functions. In newer therapeutic approaches, modulation of the actual production of such proteins is desired. By interfering with the production of proteins, the maximum therapeutic effect might be obtained with minimal side effects. It is the general object of such therapeutic approaches to interfere with or otherwise modulate gene expression which would lead to undesired protein formation.

One method for inhibiting specific gene expression is with the use of oligonucleotides, especially oligonucleotides which are complementary to a specific target messenger RNA (mRNA) sequence. Several oligonucleotides are currently undergoing clinical trials for such use.

Transcription factors interact with double-stranded DNA during regulation of transcription. Oligonucleotides can serve as competitive inhibitors of transcription factors to modulate the action of transcription factors. Several recent reports describe such interactions (see Bielinska, A., et. al., *Science*, 1990, 250, 997–1000; and Wu, H., et. al., *Gene*, 1990, 89, 203–209).

In addition to such use as both indirect and direct regulators of proteins, oligonucleotides have also found use in diagnostic tests. Such diagnostic tests can be performed using biological fluids, tissues, intact cells or isolated cellular components. As with gene expression inhibition, diagnostic applications utilize the ability of oligonucleotides to hybridize with a complementary strand of nucleic acid. Hybridization is the sequence specific hydrogen bonding of oligonucleotides via Watson-Crick and/or Hoogsteen base pairs to RNA or DNA. The bases of such base pairs are said to be complementary to one another.

Oligonucleotides are also widely used as research reagents. They are useful for understanding the function of many other biological molecules as well as in the preparation of other biological molecules. For example, the use of oligonucleotides as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies and genetic counseling. Commercialization has led to the development of kits which assist non-molecular biology-trained personnel in applying PCR. Oligonucleotides, both natural and synthetic, are employed as primers in PCR technology.

Oligonucleotides are also used in other laboratory procedures. Several of these uses are described in common laboratory manuals such as *Molecular Cloning, A Laboratory Manual*, Second Ed., J. Sambrook, et al., Eds., Cold Spring Harbor Laboratory Press, 1989; and *Current Protocols In Molecular Biology*, F. M. Ausubel, et al., Eds., Current Publications, 1993. Such uses include Synthetic Oligonucleotide Probes, Screening Expression Libraries with Antibodies and Oligonucleotides, DNA Sequencing, In Vitro Amplification of DNA by the Polymerase Chain Reaction and Site-directed Mutagenesis of Cloned DNA (see Book 2 of Molecular Cloning, A Laboratory Manual, ibid.) and DNA-Protein Interactions and The Polymerase Chain Reaction (see Vol. 2 of Current Protocols In Molecular Biology, ibid).

Oligonucleotides can be synthesized to have custom properties that are tailored for a desired use. Thus a number of chemical modifications have been introduced into oligonucleotides to increase their usefulness in diagnostics, as research reagents and as therapeutic entities. Such modifications include those designed to increase binding to a target strand (i.e. increase their melting temperatures, (Tm)); to assist in identification of the oligonucleotide or an oligonucleotide-target complex; to increase cell penetration; to stabilize against nucleases and other enzymes that degrade or interfere with the structure or activity of the oligonucleotides; to provide a mode of disruption (terminating event) once sequence-specifically bound to a target; and to improve the pharmacokinetic properties of the oligonucleotides.

Thus, it is of increasing value to prepare oligonucleotides and other phosphate linked oligomers for use in basic research or for diagnostic or therapeutic applications. Consequently, and in view of the considerable expense and time required for synthesis of specific oligonucleotides, there has been a longstanding effort to develop successful methodologies for the preparation of specific oligonucleotides with increased efficiency and product purity.

Synthesis of oligonucleotides can be accomplished using both solution phase and solid phase chemistries. Oligonucleotide synthesis via solution phase in turn can be accomplished with several coupling chemistries. However, solution phase chemistry requires purification after each internucleotide coupling, which is labor intensive and time consuming.

The current method of choice for the preparation of naturally occurring oligonucleotides, as well as modified oligonucleotides such as phosphorothioate and phosphorodithioate oligonucleotides, is via solid-phase synthesis wherein an oligonucleotide is prepared on a polymer support (a solid support) such as controlled pore glass (CPG); oxalyl-controlled pore glass ( see, e.g., Alul, et al., Nucleic Acids Research 1991, 19, 1527); TENTAGEL Support, (see, e.g., Wright, et al., Tetrahedron Letters 1993, 34, 3373); or POROS, a polystyrene resin available from Perceptive Biosystems.

Solid-phase synthesis relies on sequential addition of nucleotides to one end of a growing oligonucleotide chain. Typically, a first nucleoside (having protecting groups on any exocyclic amine functionalities present) is attached to an appropriate glass bead support and activated phosphite compounds (typically nucleotide phosphoramidites, also bearing appropriate protecting groups) are added stepwise to elongate the growing oligonucleotide. The nucleotide phosphoramidites are reacted with the growing oligonucleotide using the principles of a "fluidized bed" for mixing of the reagents. The known silica supports suitable for anchoring the oligonucleotide are very fragile and thus cannot be exposed to aggressive mixing. Brill, W. K. D., et al. *J. Am. Chem. Soc.*, 1989, 111, 2321, disclosed a procedure wherein an aryl mercaptan is substituted for the nucleotide phosphoramidite to prepare phosphorodithioate oligonucleotides on glass supports.

Additional methodologies utilizing solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069. In these and other solid-phase procedures the oligonucleotide is synthesized as an elongating strand. However, the number of individual strands that can be anchored to a unit surface area of the support is limited. Also, the activated nucleotides that are added to the growing oligonucleotide are relatively expensive and must be used in stoichiometric excess.

While presently-utilized solid-phase syntheses are very useful for preparing small quantities of oligonucleotide, i.e., from about the $\mu$mol to mmol range, they typically are not amenable to the preparation of the larger quantities of oligonucleotides necessary for biophysical studies, preclinical and clinical trials and commercial production. Currently, to synthesize more than about three fourths of a mmol of oligonucleotide it is necessary to do sequential syntheses. A general review of solid-phase versus solution-phase oligonucleotide synthesis is given in the background section of Urdea, et al. U.S. Pat. No. 4,517,338, entitled "Multiple Reactor System And Method For Oligonucleotide Synthesis"

Solution-phase synthetic oligonucleotide techniques should be useful for large scale preparation. One such solution phase preparation utilizes phosphorus triesters. As reported in Yau, E. K., et.al., Tetrahedron Letters, 1990, 31, 1953, the triester oligonucleotide approach was used to prepare thymidine dinucleoside and thymidine dinucleotide phosphorodithioates. The phosphorylated thymidine nucleoside intermediates utilized in this approach were obtained by treatment of commercially available 5'-O-dimethoxytritylthymidine-3'-[($\beta$-cyanoethyl)-N,N-diisopropyl]-phosphoramidite first with either 4-chloro or 2,4-dichlorobenzylmercaptan and tetrazole, and then a saturated sulfur solution. The resulting phosphorodithioate nucleotide was then reacted via the triester synthesis method with a further thymidine nucleoside having a free 5'-hydroxyl.

Brill, W. K. D., et.al., *J. Am. Chem. Soc.*, 1991, 113, 3972, recently disclosed that treatment of a phosphoramidite such as N,N-diisopropyl phosphoramidite with a mercaptan such as 4-chloro or 2,4-dichlorobenzylmercaptan in the presence of tetrazole yields a derivative suitable for preparation of a phosphorodithioate as a major product and a derivative suitable for preparation of a phosphorothioate as a minor product.

Further details of methods useful for preparing oligonucleotides may be found in Sekine, M., etc al., *J. Org. Chem.*, 1979, 44, 2325; Dahl, O., Sulfur Reports, 1991, 11, 167– 192; Kresse, J., et.al., Nucleic Acids Research, 1975, 2, 1–9; Eckstein, F., *Ann. Rev. Biochem.*, 1985, 54, 367–402; and Yau, E. K. U.S. Pat. No. 5,210,264 entitled "S-(2,4-Dichlorobenzyl)-$\beta$ -Cyanoethyl Phosphorothioate Diester".

Although phosphorothioates and other oligonucleotides are of great utility, the art suggests no large scale techniques for their preparation. Accordingly, there remains a long-felt need for such methods, and particularly for methods having improved efficiency.

The yield improvements obtained with the present invention are achieved specifically with regard to the deblocking procedures for the 5' hydroxyl group and in less frequently the 3' hydroxyl group of the oligonucleotide being synthesized, and more particularly with regard to the use of a carbocation scavenging agent for any one or more of the protecting groups conventionally used for blocking the 5' hydroxyl and 3' hydroxyl groups. The use of such a scavenging agent has not been suggested heretofore in the art concerning synthesis of oligonucleotides, such as is represented by the technical literature and U.S. patents set out further above. The level of yield improvement which has been achieved with the use of such scavenging agents is all the more surprising in view of the longstanding conventional use of protecting groups such as dimethoxytrityl and other similar groups.

Although scavenging groups have been used with trityl blocking groups in syntheses which are in no way analogous to the oligonucleotide syntheses described above, it was an unexpected discovery that it was possible to achieve significant increases in yield by using such scavenging agents with trityl blocking groups in the synthesis of oligonucleotides. Representative of such non-analogous art is the following:

Mehta, A., et al., *Tetrahedron Letters*, 1992, 33, 5441–5444, discloses improved selectivity of deprotection of Boc and related t -butyl -containing protecting groups in peptide synthesis, where deprotection is by trifluoroacetic acidmediated acidolysis, through the use of triethylsilane and other carbocation scavengers;

Kemp, D. S., et al., *J. Peptide Protein Res.*, 1998, 31, 359–372, discloses a study of the deblocking of N-a-Bpoc peptides in dichloromethane containing 0.5% trifluoroacetic acid, which found that only indole, benzenethiol, and benzyl mercaptan showed moderate reactivity as carbocation scavengers, while phenol, resorcinol, 1,3 -dimethoxybenzene, 1,3,5 -trimethoxybenzene, and dimethyl sulfide were inefficient.

Pearson, D. A., et al., Tetrahedron Letters, 1989, 30, 2739–2742, discloses the use of triethylsilane and triisopropylsilane as carbocation scavengers in the acidic deblocking of trityl blocked sulfhydryl groups in peptide synthesis.

Brenner, D., et al., *Inorg. Chem.*, 1984, 23, 3793–3797, and U.S. Pat. No. 4,673,562, discloses the use of triethylsilane during trifluoroacetic acid deblocking of a trityl protected mercaptoacetic acid derivative in a step for preparing oxotechnium (V) diamido dithioates.

OBJECTS OF THE INVENTION

It is an object of this invention to provide improved methods for the synthesis of oligonucleotides that are used in diagnostics, therapeutics and as research reagents.

This and other objects will become apparent to persons of ordinary skill in the art from a review of the present specification and appended claims.

SUMMARY OF THE INVENTION

In accordance with the present invention there is provided an improved method for the preparation of oligonucleotides. According to the method a protected nucleoside is attached to a solid support, the nucleoside being protected at the 5'-O hydroxyl position with an acid labile protecting group that forms a carbocation upon cleavage with acid. The 5' protecting group is the removed with an acidic solution containing a carbocation scavenging agent to give the free 5' hydroxyl. The solid support is then washed to remove excess acid solution and scavenged carbocation, and the free 5' hydroxyl is reacted in the presence of a catalyst with a nucleotide containing an active phosphite. The phosphite is oxidized to a phosphate, and remaining reactive sites are capped with a solution containing an acid anhydride. The 5'-protecting group is then removed (deblocked) as before, and the sequence of steps repeated at least once for subsequent couplings of additional nucleotides. The oligonucleotide is then cleaved from the solid support. In some preferred embodiments capping is performed before the oxidation.

In accordance with the present invention there also is provided an improved process for the synthesis of a oligonucleotide including selecting a nucleoside protected at the 3' hydroxyl position with a base labile protecting group and further protected at the 5' hydroxyl position with an acid labile protecting group that forms a carbocation upon cleavage with acid. The 5' hydroxyl protecting group is removed with an acidic solution containing a carbocation scavenging agent. The resulting free 5' hydroxyl group is reacted in the presence of a catalyst with a nucleotide containing an active phosphite. The phosphite is oxidized to a phosphate as for instance using a solution containing iodine. Capping of the remaining reactive sites is effected with a solution containing an acid anhydride. The steps are repeated at least once for subsequent couplings of additional nucleotides, and the 3' hydroxyl base labile protecting group is cleaved with base. In some preferred embodiments capping is performed prior to oxidation.

Preferred carbocation scavenging agents for use in the methods of the invention include anisole, thioanisole, benzyl mercaptan, ethanediol, pyrrole, substituted pyrrole, and $R_3BSiR'$; where $R_3$ is $C_1-C_4$-alkyl, phenyl or phenyl monosubstituted by halo, nitro or $C_1-C_4$-alkyl; and R' is H or halo. Triethylsilane is especially preferred.

In preferred embodiments the carbocation scavenging agent is present in the deblocking solution in the amount of from 1 to 25%, with from 1 to 10% being especially preferred and more preferably from 4 to 6 percent.

Preferred acid labile protecting groups for use in the methods of the invention include trityl, monomethoxy trityl, dimethoxy trityl, 9-phenylxanthine-9-yl (Pixyl) or 9-(p-methoxyphenyl)xanthine- 9-yl MOX).

In preferred embodiments the methods of the invention are used in the preparation of phosphate linked oligomers and oligonucleotides by the phosphoramidite, phosphotriester or H-phosphonate processes.

In another embodiment of the invention a method is provided for the preparation a phosphate linked oligomer, wherein a primary or secondary hydroxyl of the phosphate linked oligomer is blocked by an acid labile protecting group that releases an active carbocation species upon treatment with an acid; wherein the protecting group is removed with an acidic solution containing a carbocation scavenging agent.

In a further embodiment of the invention a method is provided for preparing an oligonucleotide, including protecting a 5' hydroxyl or 3' hydroxyl group of the ribose or deoxyribose portion of a 5' of 3' terminal nucleoside of the oligonucleotide with an acid labile protecting group that releases a carbocation when treated with acid, and removing the carbocation by the addition of a carbocation scavenging agent.

DETAILED DESCRIPTION OF THE INVENTION

The present invention provides methods for the preparation of oligonucleotides and phosphate linked oligomers wherein a carbocation scavenging agent is employed to suppress deleterious effects of carbocations generated during deblocking steps. The methods of the invention have greater yields and increased efficiency relative to synthesis methods currently employed in the art.

Standard solid phase oligonucleotide synthesis using phosphite triester chemistry begins covalent attachment of a 5'-O protected nucleoside to a solid support through the nucleoside 3'-oxygen. Any exocyclic amino groups present on the nucleoside are also protected by protecting groups. Attachment is achieved by any of several methodologies routinely used in the art.

The 5'-O- protecting group of the support linked nucleoside is typically removed by treatment with dilute acid and washed (rinsed) from the support with anhydrous acetonitrile. A 5'-O- protected activated phosphite (typically a phosphoramidite) is then reacted with the free 5' hydroxyl of the support bound nucleoside in the presence of a catalyst, forming an internucleotide phosphite triester linkage. Phosphoramidites of numerous nucleosides and derivatized solid supports are commercially available through various companies (e.g. Applied Biosystems Inc., Millipore Corp.). Unreacted hydroxyls are capped (for example by acetylation with acetic anhydride), and the phosphite is oxidized to the phosphate (e.g., with a solution of $I_2$) to give the dimer attached to the solid support. Repeating the above steps n times increases the length of the dimer by n nucleotide units. The oligonucleotide is recovered from the solid support by cleaving the base labile succinamide linkage with concentrated ammonium hydroxide.

One characteristic of the solid phase synthesis technique is the use of labile protecting groups to protect various functional moieties during synthesis. Protecting groups are used in oligonucleotide synthesis for protection of several different types of functionality. In general, protecting groups render chemical functionality inert to specific reaction conditions and can be appended to and removed from such functionality in a molecule without substantially damaging the remainder of the molecule. See, e.g., Green and Wuts, Protective Groups in Organic Synthesis, 2d edition, John Wiley & Sons, New York, 1991. Representative hydroxyl protecting groups used for nucleic acid chemistry are described by Beaucage, et al., Tetrahedron 1992, 48, 2223. The protecting groups typically used to protect nucleotides during DNA synthesis include base labile protecting groups and acid labile protecting groups. Base labile protecting groups are used to protect the exocyclic amino groups of the heterocyclic nucleobases. This type of protection is generally achieved by acylation. Two commonly used acylating groups are benzoylchloride and isobutyrylchloride. These protecting groups are stable to the reaction conditions used during oligonucleotide synthesis and are cleaved at about equal rates during the base treatment at the end of synthesis. The second type of protection used in standard DNA synthesis is an acid labile protecting group, which is used to protect the nucleotide 5' hydroxyl during synthesis.

Hydroxyl protecting groups typically used in oligonucleotide synthesis may be represented by the following structure:

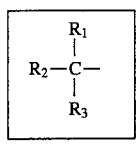

wherein each of $R_1$, $R_2$ and $R_3$ is an unsubstituted or monosubstituted aryl or heteroaryl group selected from phenyl, naphthyl, anthracyl, and five or six membered heterocylic rings with a single heteroatom selected from N, O and S, or two N heteroatoms, including quinolyl, furyl, and thienyl; where the substituent is selected from halo (i.e., F, Cl, Br, and I), nitro, $C_1$–$C_4$-alkyl or alkoxy, and aryl, aralkyl and cycloalkyl containing up to 10 carbon atoms; and wherein $R_2$ and $R_3$ may each also be $C_1$–$C_4$-alkyl or aralkyl or cycloalkyl containing up to 10 carbon atoms. Of these hydroxyl protecting groups, the triphenylmethyl (trityl), monomethoxytrityl, and dimethoxytrityl groups have been most commonly used.

The 5' hydroxyl protecting groups commonly used for DNA synthesis are dimethoxytrityl, monomethoxy trityl, trityl, and 9-phenyl -xanthene (pixyl). Dimethoxytrityl protecting groups are extremely acid labile enabling the use of a dilute acid (e. g. 3% trichloroacetic acid) to selectively remove them.

Hydroxyl protecting groups used for oligonucleotide synthesis that form stable ions with a characteristic visible absorbance spectrum are very useful for monitoring stepwise yields. The extinction coefficients are known for the more commonly used protecting groups which enables the calculation of concentration as a function of absorbance. The expected concentration of a carbocation for a given synthesis can be compared to the calculated theoretical concentration corresponding to a coupling efficiency of 100%. By adjusting the parameters (e.g. solvent, protecting group, reaction time, rinse cycles, etc.) used to synthesize a given oligonucleotide and monitoring the trityl ion, a set of parameters are determined that maximizes the overall yield.

During synthesis, coupling of a nucleotide to the solid support bound nucleoside is preceded by a deprotection (deblocking) step which releases the carbocation of the protecting group. The next step is coupling of the phosphoramidire to the deprotected 5'-O- followed by a capping step. The stepwise coupling efficiency of joining nucleotides to the growing oligonucleotide can be evaluated by comparing the amount of carbocation released during the ensuing deprotection step. This is determined spectrophotometrically by quantitating the carbocation released at Amax 498 nm at acidic pH. The coupling efficiency of a synthesis may be determined by comparing the amount of trityl released during the first coupling to that released during the last.

The deblocking, i.e., the removal of the 5'-O- protecting group, is readily accomplished using conventional means. For example, Lewis acids such as $ZnBr_2$, $AlCl_3$, $BF_3$ and $TiCl_4$ may be used in solvents such as nitromethane, tetrahydrofuran, and mixed solvents such as nitromethane and a lower alkyl alcohols, e.g., methanol. Protic acids such as acetic acid, dichloroacetic acid, trifluoroacetic acid, and toluenesulfonic acid may also be used. Dichloromethane is typical of solvents used with such protic acids. It is preferred to use mild deblocking conditions. A commonly used deblocking system utilizes 3% trichloroacetic acid in dichloromethane.

Cleavage of the initial 5'-O-protecting group proceeds in essentially quantitative fashion. However, the carbocation released is relatively long lived in dilute acid because the electron deficient carbon can be stabilized by the large π systems common to the standard protecting groups. The carbocation is an active species that can react with the solid support or any hydroxyl groups including the hydroxyl groups that were deprotected. A carbocation reacting with a 5' hydroxyl will reprotect that position, making that position unavailable for coupling to the next nucleotide. If this growing oligonucleotide chain undergoes all the remaining couplings successfully the resulting oligonucleotide will be an n-1 short sequence wherein n-1 is the number of nucleotides in the full length oligonucleotide. Thus, carbocation interaction with the solid support can result in shortened oligomers.

One example of the interaction of carbocation and support is the trityl group, the cation of which has a weak affinity for polystyrene. See Pless, R. C. and Letsinger, R. L., *Nucleic Acids Research*, 1975, 2:773. During oligonucleotide synthesis on polystyrene/polyethylene graft polymer supports, trityl cation retention on the support (so-called "trityl sticking") has also been observed.

As bed volume increases, the tendency for retritylation of hydroxyl sites becomes of increasing concern. As other sites in an oligonucleotide are acid sensitive (e.g., adenine bases, which may become depurinated) resorting to larger volumes of acid wash is not always a viable solution. Short sequences are an inherent byproduct of presently practiced solid phase oligonucleotide synthesis, and, in current synthetic protocols, they must be separated from the desired oligonucleotide by chromatography, leading to considerable reduction in yield. The removal of carbocations produced during deblocking therefore increases yield and synthetic efficiency.

It is therefore desirable to quench (i.e., remove) the active species immediately after it is formed. This is achieved according to the methods of the invention by using a carbocation scavenging agent. A carbocation scavenging agent will remove the carbocation by reductively transforming it into a neutral species. The reductive transformation is believed to occur by the addition of hydrogen to carbon, thereby forming the neutral species. The neutral species will not reprotect free hydroxyl groups, thus affording quantitative and nonreversible deprotection.

Deprotection without the use of a scavenger can be interpreted as an equilibrium between detritylation and retritylation. In accordance with the methods provided by the present invention, this equilibrium is interrupted by the use of a carbocation scavenging agent which enters into an irreversible reaction with the carbocation, thereby preventing retritylation. The carbocation scavenging agents used in the improved methods of the present invention are selected from anisole, thioanisole, benzyl mercaptan, ethanediol, substituted and unsubstituted pyrroles, and $R_3SiR'$, where $R_3$ is $C_1$–$C_4$-alkyl, phenyl or phenyl mono-substituted by halo, nitro or $C_1$–$C_4$-alkyl, and R' is H or halo. The preferred scavenging agent is triethylsilane. The amount of scavenger in the deblocking solution may vary between 1 and 25 percent by volume, with 1 to 10 percent being preferred and 4–6 percent being even more preferred.

Whereas trityl and other highly colored cations are very useful during preliminary synthesis on small scale to adjust reaction conditions, they become a detriment to the overall yield for large scale syntheses. This effect is more pronounced in syntheses involving large numbers of nucleotides or modified nucleotide structures, e.g. phosphate linked oligomers structures. The improved methods of the current invention find great utility in the large scale production of oligonucleotides where the improved yield is of a significant value.

The improved process of the present invention are useful in the synthesis of oligonucleotide compounds where a reactive carbocation species is present during a deblocking cycle. Included in the types of oligonucleotides that meet this criteria and are routinely synthesized are compounds including phosphodiesters, phosphotriesters, phosphorothioates, phosphodithioates, and H-phosphonates. These oligonucleotides are of the structure:

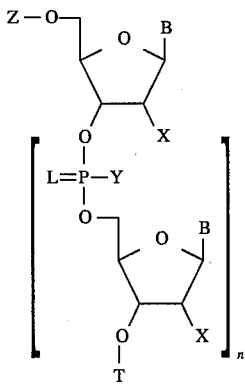

STRUCTURE I wherein Z is an acid labile protecting group from the list above. B is a nucleobase; adenine (A), cytosine (C), guanine (G), thymine (T) or uracil (U). For the phosphodiester DNA, X = H, and B= A, C, G, or T; and for the phosphodiester RNA, X = OH, and B= A, C, G or U. Y is OH or SH, and L is O or S. T is a solid support as described above for solid phase synthesis or a base labile protecting group for solution phase synthesis.

In the phosphoramidite process, a 3'-phosphite is prepared by treating a 5'-trityl blocked nucleoside with a compound such as $Pr_2N-P(OCH_2CH_2CN)_2$ in the presence of tetrazole as an activating agent. The resulting phosphite is then oxidized with sulfur and deprotected to give a nucleoside 3'- or 5'-O-phosphorothioate.

The amino moiety of the phosphoramidites of the invention can be selected from various amines presently used for such phosphoramidites. Such amines include both aliphatic and heteroaryl amines. One preferred amino group is diisopropylamino. Other examples of suitable amines as are described in various United States patents, principally those to M. Caruthers and associates. These include U.S. Pat. Nos. 4,668,777; 4,458,066; 4,415,732; and 4,500,707; all of which are herein incorporated by reference.

In addition to the amino moiety of the phosphoramidite, for phosphodiester and phosphorothioate linkages, an additional phosphorous blocking group is used. One preferred blocking group is the cyanoethyl group. Other phosphorous blocking groups include methoxy and 2-(methylsulphonyl)ethyl.

During the chain elongation step the terminal free 5' hydroxyl group of a growing nucleotide chain is coupled to an active phosphite group of an incoming nucleotide. The phosphite group is activated to nucleophilic attack by the 5' hydroxyl using an activating agent. It is believed that the activating agent displaces the amino group (e.g. diisopropyl amino) from the phosphite group, thereby activating the phosphite group to nucleophilic attack by the 5' hydroxyl group of the growing nucleotide chain. Any activating agent that can activate the phosphorous to nucleophilic attack without interacting with the growing nucleotide chain may be suitable for use with the present invention. One preferred catalyst is tetrazole. Some commonly used commercially available activating agents are thiotetrazole, nitrotetrazole, and N,N-diisopropylaminohydrotetrazolide. Other suitable activating agents are also disclosed in the above incorporated patents as well as in U.S. Pat. No. 4,725,677 and in Berner, S., Muhlegger, K., and Seliger, H., *Nucleic Acids Research* 1989, 17:853; Dahl, B. H., Nielsen, J. and Dahl, O., Nucleic Acids Research 1987, 15:1729; and Nielson, J. Marugg, J. E., Van Boom, J. H., Honnens, J., Taagaard, M. and Dahl, O., *J. Chem. Research* 1986, 26, all of which are herein incorporated by reference.

The structures listed above are representative of commonly synthesized phosphate linked oligomers, and the application of the methods of the present invention to them is illustrative, and not limiting. For example, it is known to substitute a wide variety of modifications on the above structures including base modifications, backbone modifications, phosphate modifications, sugar modifications, and 2' modifications. Recent modifications include replacing the sugar with an alternative structure which has primary and a secondary alcohol groups similar to those of ribose. As used herein, these modified compounds are collectively referred to as phosphate linked oligomers. Phosphate linked oligomers bind to native DNA and RNA by Watson/Crick pairing to corresponding, in-sequence nucleobases, but may differ from native DNA and RNA with regard to their nucleobase-like recognition moieties or backbone moieties. In some phosphate linked compounds bases are replaced by a tethered functional group. Phosphate linked oligomers are synthesized by known methods including phosphoramidite, phosphotriester and H-phosphonate processes.

Phosphate linked oligomers release an active carbocation species during the acidic deblocking cycle of chain elongation. Thus the methods of the invention are useful in the synthesis of these compounds. The improved yields which are obtained in accordance with the present invention can be achieved with respect to all of the methods used for preparing O- and S-linked oligonucleotide phosphorothioates and dithioates.

The methods of the invention are useful in the synthesis of any oligonucleotide, phosphate linked oligomer, related intermediate or starting material wherein a primary or secondary hydroxyl of the oligonucleotide, phosphate linked oligomer, related intermediate or starting material is blocked by an acid labile protecting groups which releases an active species upon treatment with acid. Using the methods of the invention various oligonucleotide O, S-phosphorodithioates, thiophosphotriesters, thiophosphoramidates, methylphosphonothioates, and cyclic phosphorothioates can be prepared in accordance with the methods of the invention with increased efficiency relative to synthetic methods presently in known in the art. Further details concerning the oligonucleotides described above may be found, e.g., in Dahl, O., *Sulfur Reports*, ibid.

As will be recognized, the process steps of the present invention need not be performed any particular number of times or in any particular sequence. Additional objects, advantages, and novel features of this invention will become apparent to those skilled in the art upon examination of the following examples thereof, which are not intended to be limiting.

EXAMPLE 1

Synthesis of 5'-TTTTTTT-3' Phosphorothioate Heptamer 50 milligrams (2 mmole) of 5'-O- dimethoxytritylthymidine bonded to CPG (controlled pore glass) through an ester linkage is placed in a glass reactor, and a dichloromethane solution of 2% dichloroacetic acid (volume/volume) and 5% triethylsilane (volume/volume) is added to deprotect the 5'-hydroxyl groups. The product is washed with acetonitrile and a 0.2 M solution of 5'-O-(4,4'-dimethoxytrityl)thymidine- 3'-O-(2-cyanoethyl-N,N-diisopropylphosphoramidite) in acetonitrile and a 0.4 M solution of 1H-tetrazole in acetonitrile is added. The reaction is allowed to proceed at room temperature for 5 minutes. The product is washed with acetonitrile, and then a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile.

This complete cycle is repeated five more times to yield the completely protected thymidine heptamer. The carrier containing the compound is treated with 30% aqueous ammonium hydroxide solution for 90 minutes at room temperature. The aqueous solution is filtered and concentrated under reduced pressure to give a phosphorothioate heptamer of TTTTTTT.

EXAMPLE 2

Synthesis of 5'-d(GACT)-3' Phosphorothioate Tetramer 50 milligrams (2 mmole) of 5'-O- dimethoxytritylthymidine bonded to CPG (controlled pore glass) through an ester linkage is placed in a glass reactor, and a dichloromethane solution of 2% dichloroacetic acid (volume/volume) and 5% triethylsilane (volume/volume) is added to deprotect the 5'-hydroxyl groups. The product is washed with acetonitrile. Then, a 0.2 M solution of 5' -O- (4,4'-dimethoxytrityl) thymidine-3 ' -O- (2 -cyanoethyl-N,N-diisopropylphosphoramidite) in acetonitrile and a 0.4 M solution of 1H-tetrazole in acetonitrile is added, and allowed to react at room temperature for 5 minutes. The product is washed with acetonitrile, and then a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl groups. The product is washed with acetonitrile.

A solution of 2% dichloroacetic acid (volume/volume) and 5% triethylsilane (volume/volume) is added to deprotect the 5'-hydroxyl groups. The product is washed with acetonitrile. Then, a 0.2 M solution of N-4-benzoyl-5'-O-(4,4'-dimethoxytrityl)- 2'-deoxycytidine-3'-O-(2-cyanoethyl-N,N-diisopropylphosphoramidite) in acetonitrile and a 0.4 M solution of 1H-tetrazole in acetonitrile is added, and allowed to react at room temperature for 5 minutes. The product is washed with acetonitrile, and then a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl groups. The product is washed with acetonitrile.

A solution of 2% dichloroacetic acid (volume/volume) and 5% triethylsilane (volume/volume) is added to deprotect the 5'-hydroxyl groups. The product is washed with acetonitrile. Then, a 0.2 M solution of N-6-benzoyl-5'-O-(4,4'-dimethoxytrityl)- 2'-deoxyadenosine-3'-O-(2-cyanoethyl-N,N'-diisopropylphosphoramidite) in anhydrous acetonitrile and a 0.4 M solution of 1H-tetrazole in acetonitrile is added and allowed to react at room temperature for 5 minutes. The product is washed with acetonitrile, and then a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl groups. The product is washed with acetonitrile.

A solution of 2% dichloroacetic acid (volume/volume) and 5% triethylsilane (volume/volume) is added to deprotect the 5'-hydroxyl groups. The product is washed with acetonitrile. Then a 0.2 M solution of N-2-isobutyryl-5'-O-(4,4'-dimethoxytrityl)- 2'-deoxyguanosine-3'-O-(2-cyanoethy-N,N'-diisopropylphosphoramidite) in acetonitrile and a 0.4 M solution of 1H-tetrazole in acetonitrile is added and allowed to react at room temperature for 5 minutes. The product is washed with acetonitrile and then a 0.05 M solution of Beaucage reagent in acetonitrile is added and allowed to react at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl groups. The product is washed with acetonitrile.

The carrier containing the compound is treated with 30% aqueous ammonium hydroxide solution for 90 minutes at room temperature and then incubated at 55° C. for 24 hour. The aqueous solution is filtered and concentrated under reduced pressure to give a phosphorothioate tetramer of 5'-dG-dA-dC-T- 3'.

EXAMPLE 3

Synthesis of 5'-TTTTTTT-3' Phosphodiester Heptamer 50 milligrams (2 mmole) of 5 '-O-dimethoxytritylthymidine bonded to CPG (controlled pore glass) through an ester linkage is placed in a glass reactor, and a dichloromethane solution of 2% dichloroacetic acid (volume/volume) and 5% triethylsilane (volume/volume) is added to deprotect the 5'-hydroxyl groups. The product is washed with acetonitrile. Then a 0.2 M solution of 5'-O- (4,4 '-dimethoxytrityl) thymidine-3 '-O- (2-cyanoethyl-N,N-diisopropylphosphoramidite) in acetonitrile and a 0.4 M solution of 1H-tetrazole in acetonitrile is added and allowed to react at room temperature for 5 minutes. The product is washed with acetonitrile and then a solution of iodine (composed of iodine, water, lutidine and tetrahydrofuran) is added and allowed to react at room temperature for 5 minutes. This oxidation step is repeated one more time for 5 minutes. The support is washed with acetonitrile and then a solution of acetic anhydride/lutidine/THF (1:1:8), and N-methyl imidazole/THF is added to cap the unreacted 5'-hydroxyl groups. The product is washed with acetonitrile.

This complete cycle is repeated five more times to yield the completely protected thymidine heptamer. The carrier containing the compound is treated with 30% aqueous ammonium hydroxide solution for 90 minutes at room temperature. The aqueous solution is filtered and concentrated under reduced pressure to give a phosphorothioate heptamer of TTTTTTT.

EXAMPLE 4

Synthesis of 5'-d(GACT)-3' Phosphodiester Tetramer 50 milligrams (2 mmole) of 5'-O- dimethoxytritylthymidine bonded to CPG (controlled pore glass) through an ester linkage is placed in a glass reactor and a dichloromethane solution of 2% dichloroacetic acid (volume/volume) and 5% triethylsilane (volume/volume) is added to deprotect the 5'-hydroxyl groups. The product is washed with acetonitrile. Then a 0.2 M solution of 5'-O- (4,4 '-dimethoxytrityl) thymidine-3' -O- (2-cyanoethyl-N,N-diisopropylphosphoramidite) in acetonitrile and a 0.4 M solution of 1H-tetrazole in acetonitrile is added and allowed to react at room temperature for 5 minutes. The product is washed with acetonitrile and then a solution of iodine (composed of iodine, water, lutidine and tetrahydrofuran) is added and allowed to react at room temperature for 5 minutes. This oxidation step is repeated one more time for 5 minutes. The support is washed with acetonitrile and then a solution of acetic anhydride/lutidine/THF (1:1:8), and N-methyl imidazole/THF is added to cap the unreacted 5'-hydroxyl groups. The product is washed with acetonitrile.

A solution of 2% dichloroacetic acid (volume/volume) and 5% triethylsilane (volume/volume) is added to deprotect the 5'-hydroxyl groups. The product is washed with acetonitrile. Then a 0.2 M solution of N-4-benzoyl-5'-O- (4,4'-dimethoxytrityl) -2'-deoxycytidine -3'-O- (2 -cyanoethyl -N, N-diisopropylphosphoramidite) in acetonitrile and a 0.4 M solution of 1H-tetrazole in acetonitrile is added and allowed to react at room temperature for 5 minutes. The product is washed with acetonitrile, and then a solution of iodine (composed of iodine, water, lutidine and tetrahydrofuran) is added and reacted at room temperature for 5 minutes. This oxidation step is repeated one more time for 5 minutes. The support is washed with acetonitrile and then a solution of acetic anhydride/ lutidine/THF (1:1:8) and N-methyl imidazole/THF is added to cap the unreacted 5'-hydroxyl groups. The product is washed with acetonitrile.

A solution of 2% dichloroacetic acid (volume/volume) and 5% triethylsilane (volume/volume) is added to deprotect the 5'-hydroxyl groups. The product is washed with acetonitrile. Then a 0.2 M solution of N-6-benzoyl-5'-O-(4,4'-dimethoxytrityl)- 2'-deoxyadenosine-3'-O-(2-cyanoethyl-N, N-diisopropylphosphoramidite) in anhydrous acetonitrile and a 0.4 M solution of 1H-tetrazole in acetonitrile is added, and allowed to react at room temperature for 5 minutes. The product is washed with acetonitrile and then a solution of iodine (composed of iodine, water, lutidine and tetrahydrofuran) is added and reacted at room temperature for 5 minutes. This oxidation step is repeated one more time for 5 minutes. The support is washed with acetonitrile and then a solution of acetic anhydride/lutidine/THF (1:1:8), and N-methyl imidazole/THF is added to cap the unreacted 5'-hydroxyl groups. The product is washed with acetonitrile.

A solution of 2% dichloroacetic acid (volume/volume) and 5% triethylsilane (volume/volume) is added to deprotect the 5'-hydroxyl groups. The product is washed with acetonitrile. Then a 0.2 M solution of N-2-isobutyryl-5'-O-(4,4'-dimethoxytrityl)- 2'-deoxyguanosine-3'-O-(2-cyanoethyl-N, N'-diisopropylphosphoramidite) in acetonitrile and a 0.4 M solution of 1H-tetrazole in acetonitrile is added and allowed to react at room temperature for 5 minutes. The product is washed with acetonitrile and then a solution of iodine (composed of iodine, water, lutidine and tetrahydrofuran) is added and reacted at room temperature for 5 minutes. This oxidation step is repeated one more time for 5 minutes. The support is washed with acetonitrile and then a solution of acetic anhydride/lutidine/THF (1:1:8) and N-methyl imidazole/THF is added to cap the unreacted 5'-hydroxyl groups. The product is washed with acetonitrile.

The carrier containing the compound is treated with 30% aqueous ammonium hydroxide solution for 90 minutes at room temperature and then incubated at 55° C. for 24 hour. The aqueous solution is filtered and concentrated under reduced pressure to give a phosphorothioate tetramer of 5'-dG-dA-dC-T- 3'.

EXAMPLE 5

Synthesis of 5 ' -TTTTTTT- 3 ' Phosphodiester Heptamer 50 milligram (2 mmole) of 5'-O-dimethoxytritylthymidine bonded to CPG (controlled pore glass) through an ester linkage is placed in a glass reactor, and a dichloromethane solution of 2% dichloroacetic acid (volume/volume) and 5% triethylsilane (volume/volume) is added to deprotect the 5'-hydroxyl groups. The product is washed with acetonitrile. Then the product is washed with a mixture of acetonitrile and pyridine. A solution of 5'-O- (4,4'-dimethoxytrityl)thymidine- 3' nucleotide H-phosphonate monomer and an activator is then added and allowed to react at room temperature for 2 minutes. The product is washed with acetonitrile. This complete cycle is repeated five more times and after the oligomer assembly is complete the resulting H-phosphonate oligomer is oxidized with aqueous iodine and incubated with aqueous ammonia to afford phosphodiester heptamer of TTTTTTT.

EXAMPLE 6

1-(1-Thymine)-2,3-propandiol

To a stirred solution of thymine (4.2 g, 33 mmol) in dry dimethylformamide (DMF, 30 ml) was added R-(+)-glycidol (2.2 g, 30 mmol), and potassium carbonate (50 mg, 0.36 mmol). The suspension was heated to 80° C. for five hours then evaporated. The products were diluted with methanol (25 ml) and filtered. The filtrate was evaporated and the residue purified by silica gel column chromatography. Elution with ethyl acetate:methanol (9:1, v/v), pooling of appropriate fractions, and evaporation furnished the N(1) substituted material free from N(1),N(3) disubstituted material to yield 3.08g (60%). $^1$H NMR (DMSO-d$_6$): δ, 1.8 (s, 3, CH$_3$); 3.35 (bm, 3, C$\underline{H}$OHC$\underline{H}_2$OH); 3.7 and 3.9 (2 m, 2, NCH $_2$); 4.7 (bs, 1, CH$_2$O$\underline{H}$, exchanges with D$_2$O); 5.0 (bs, 1, CHO $\underline{H}$, exchanges with D$_2$O); 7.4 (s, 1, H-6); 11.2 (bs, 1, NH, exchanges with D$_2$O) . Anal. calcd. for C$_8$H$_{12}$N$_2$O$_4$ (200.193): 47.99% C, 6.04% H, 13.99% N; found: 47.35% C 6.10% H, 13.67% N.

EXAMPLE 7

1 -(1-Thyrmine)-3-O- dimethoxytrityl-2-propanol

To a stirred solution of 1- (1-thymine) -2,3 -propandiol (2.079 g, 12.4 mmol) in dry pyridine (30 ml) was added 4,4'-dimethoxytrityl chloride (4.4 g, 13 mmol) . The suspension was stirred at room temperature for four hours. The reaction mixture was evaporated and the residue purified by silica gel column chromatography. Elution with ethyl acetate:hexane:triethylamine (3/2/1, v/v/%), pooling of appropriate fractions, and evaporation gave a yield of 3.39 g (54%). $^1$H NMR (DMSO-d$_6$): δ1.8 ( s, 3, CH$_3$); 2.9 (m, 2, CH$_2$ODMT); 3.8 (s, 6, OCH$_3$); 3.9 (m, 2, NCH$_2$); 5.3 (d, 1, OH, exchanges with D$_2$O); 6.9 (m, 4, trityl); 7.3 (m, 9, trityl); 11.2 (s, 1, NH, exchanges with D$_2$O).

EXAMPLE 8

1- (1-Thymine)-3-O-dimethoxytrityl-2-O-[ (N, N-diisopropylamino)-2-cyanoethoxyphosphite]propane A stirred solution of 1-(1-thymine)-3-O-dimethoxytrityl -2-propanol (3.39 g, 6.7 mmol) and N,N-diisopropylethyl amine (2.4 ml, 14 mmol) in dry THF (35 ml) was cooled to 10° C. in an ice bath. Chloro-β-cyanoethoxy-N,N-diisopropylaminophosphine ( 1.5 ml, 6.7 mmol ) was added. After stirring at room temperature for four hours the reaction mixture was evaporated and the residue purified by silica gel column chromatography. Elution with ethyl acetate: hexane: triethylamine (1:1:1, v/v/% ), pooling of appropriate fractions, and evaporation gave a yield of 2.78 g (61%). $^1$H NMR (CD$_3$CN): δ1.2 (m, 12, 6 CH$_3$); 1.75 (d, 3, CH$_3$ ); 2.45 and 2.6 (2 t, 2, CH$_2$ODMT); 3.8 (d, 6, OCH$_3$); 6.9 and 7.3 (2 m, 14, trityl); 9.3 (bs, 1, NH, exchanges with D$_2$O). $^{31}$P NMR (CD$_3$CN): δ, 150.19 and 150.66. Anal. calcd. for C$_{38}$H$_{47}$N$_4$O$_7$P (702.786): 64.94% C, 6.74% H, 7.97% N; found: 64.60% C, 6.91% H, 7.80% N.

EXAMPLE 9

Synthesis of 5'-XXXXXXT-3' Phosphate Linked Heptamer 50 milligram (2 mmole) of 5'-0dimethoxytritylthymidine bonded to CPG (controlled pore glass) through an ester linkage is placed in a glass reactor, and a dichloromethane solution of 2% dichloroacetic acid (volume/volume) and 5% triethylsilane (volume/volume) is added to deprotect the 5'-hydroxyl groups. The product is washed with acetonitrile. A solution of 1-(1-thymine)-3-O-dimethoxytrityl- 2-O-[(N, N-diisopropylamino)-2-cyanoethoxyphosphite] propane monomer and a 0.4 M solution of 1H-tetrazole in acetonitrile is then added and allowed to react at room temperature for 2 minutes. The product is washed with acetonitrile and then a solution of iodine (composed of iodine, water, lutidine and tetrahydrofuran) is added and allowed to react at room temperature for 5 minutes. This oxidation step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile. This complete cycle is repeated five more times resulting in the phosphate triester oligomer. The carrier containing the compound is treated with 30% aqueous ammonium hydroxide solution for 90 minutes at room temperature to give the phosphodiester heptamer of XXXXXXT where X represents the 1-(1-thymine)2-phosphate-3-O-propane residue.

EXAMPLE 10

Synthesis of 5'-XXXXXXT-3' Phosphate Linked Heptamer a. The process of Example 9 is repeated with the exception that anisole is used as the carbocation scavenging agent during the deprotection step.

b. The process of Example 9 is repeated with the exception that thioanisole is used as the carbocation scavenging agent during the deprotection step.

c. The process of Example 9 is repeated with the exception that benzyl mercaptan is used as the carbocation scavenging agent during the deprotection step.

d. The process of Example 9 is repeated with the exception that ethanediol is used as the carbocation scavenging agent during the deprotection step.

EXAMPLE 11

N-Fmoc-trans-4-hydroxy-L-proline

Hydroxyproline (5.00 g, 38.2 mmol) and NaHCO$_3$ (8.00 g, 95.2 mmol) were suspended in 150 ml H$_2$O/Dioxane (1:1). Fluorenylmethyl chloroformate (11.4 g, 44.0 mmol) in 25 ml toluene was added dropwise. The temperature of the reaction was not allowed to rise above 25° C. during the addition. The mixture was stirred vigorously overnight, and then quenched with 50 ml saturated NaHCO$_3$ solution and 50 ml water. The solution was then extracted with 100 ml diethyl ether. The aqueous layer was acidified to pH 1 with concentrated HCl, and extracted twice with ethyl acetate, and the organic extracts washed with brine. The solution was dried with MgSO$_4$, filtered and the solvent removed in vacuo. The pure product crystallized from the concentrated solution. Yield: 13.4 g (100%). $^1$H NMR: (CDCl$_3$, 200 MHz) δ7.75–7.15 (8H, m, ArH) , 4.55–4.05 (5H, m, ArCHCH$_2$, H2, H4), 3.65–3.45 (2H, m, 2 H5), 2.35–2.10 (2H, m, 2 H3).

EXAMPLE 12

N$^1$-Fmoc-3-hydroxypyrrolidine-5-methanol

To a solution of N-fmoc-trans-4-hydroxy-L-proline (13.4 g, 38.1 mmol) in 250 ml THF was added borane-methyl sulfide (78 mmol, 5.78 g, 7.22 ml) dropwise at room temperature. After the evolution of H$_2$ had ceased, the solution was heated to reflux with mechanical stirring. After 1 hour a white precipitate had formed. Methanol was carefully added, and the resulting solution refluxed for a further 15 minutes. The solution was cooled to room temperature, the solvents evaporated under reduced pressure, and the residual gum coevaporated with 2×100 ml methanol (MeOH). The resulting crystalline product weighed 12.0 g (35.3 mmol, 93%). $^1$H NMR: (CDCl$_{3, 200}$ MHz) δ7.85–7.25 (8H, m, ArH) , 4.50–4.10 (5H, m, ArCHCH$_2$, H3, H5), 3.80–3.40 (4H, m, 2 H2, 2 H6), 2.15–1.95 (1H, m, H2a), 1.80–1.60 (1H, m, H2b).

EXAMPLE 13

N$^1$-Fmoc-5-dimethoxytrityloxymethyl-3-hydroxypyrrolidine

The diol N$^1$-fmoc-3-hydroxypyrrolidine-5-methanol (12.0 g, 35.3 mmol) was coevaporated with dry pyridine (2×50 ml), redissolved in 200 ml dry pyridine, and cooled in an ice bath. Dimethoxytrityl chloride (13.6 g, 38 mmol) was added in portions over 15 minutes, and the solution stirred at room temperature overnight. Methanol was then added (10 ml), and the solvent removed under reduced pressure. The resulting gum was redissolved in toluene (100 ml), filtered to remove the pyridinium hydrochloride and taken to dryness again. The residue was triturated with ether/hexane to produce a tan solid, and chromatographed (0 to 1.5%

MeOH/C₂Cl₂) to give the product (14.85 g, 23 mmol, 66%). Alternatively, the product could be crystallized from 2:1 hexane/ethyl acetate.

EXAMPLE 14

5-Dimethoxytrityloxymethyl-3-hydroxypyrrolidine

To a solution of carbamate N¹fmoc-5-dimethoxytrityloxymethyl- 3-hydroxypyrrolidine (3.40 g, 5.30 mmol) in 15 ml DMF was added piperidine (1.09 ml, 0.935 g, 11.0 mmol). The solution was stirred at room temperature for 1 hour, water (100 ml) added, and the aqueous solution extracted with ethyl acetate (2×75 ml). The organic extracts were washed with aqueous NaHCO₃, brine, dried with MgSO₄ and evaporated. The residue was purified by flash using a gradient of 1→3% MeOH in CH₂Cl₂ containing 0.5% triethylamine. Pure product was obtained (1.86 g, 84%). ¹H NMR: (CDCl₃, 200 MHz) δ7.42–6.80 (13 H, ArH), 4,35 (1H, m, H5), 3.77 (6H, s, 2 OCH₃), 3.62 (1H, m, H3), 3.13–2.88 (4H, m, 2 H6, 2 H2), 1.87 (1H, q, H4a), 1.65 (1H, m, H4b).

EXAMPLE 15

N=-Palmitoyl-5-dimethoxytrityloxymethyl-3-hydroxypyrrolidine

To the amino alcohol 5-Dimethoxytrityloxymethyl-3-Hydroxypyrrolidine (0.50 g, 1.19 mmol) dissolved in 5 ml dry pyridine was added chlorotrimethylsilane (0.227 ml, 194 mg, 1.79 mmol), with stirring for 1 hour. The carboxylic acid component (e.g. palmitic acid, 359 mg, 1.40 mmol), hydroxybenzotriazole (209 mg, 1.55 mmol) and dimethylaminopropylethylcarbodiimide (EDC) (281 mg, 1.80 mmol) were dissolved in 5 ml DMF (if necessary 5 ml CH₂Cl₂ co-solvent added) and stirred for 1 hour. This solution was then added to the pyridine solution of 5, and the solution stirred until complete disappearance of the starting material. The reaction was stopped by addition of 5 ml sat NaHCO₃ and after 15 minutes the solution was diluted with water (100 ml), extracted with ethyl acetate (2×75 ml), washed with NaHCO₃, brine, dried and evaporated. The product was purified by silica gel chromatography using ethyl acetate/hexane (EtOAc/Hex) as eluant. ¹H NMR: (CDCl₃, 200 MHz) (2 rotamers, 3'-O-TMS) δ7.43–7.13, 6.88–6.74 (13 Ar-H), 4.67, 4.51, 4.40, 4.13 (4 m, 2H, H3, H5), 3.90–3.67 (m, 1H, H2a), 3.80 (s, 6H, OCH₃), 3.45 (m, 2H, H2b, H6a), 3.12 (m, 1H, H6b), 2.34–1.78 (m, 4H, H4a, H4b, COCH₂), 1.65, 1.25 (2 s, 26 H, CH₂), 0.87 (t, CH₃), 0.10 (s, 9H, OSi (CH₃)₃).

EXAMPLE 16

N¹-Palmitoyl-5-dimethoxytrityloxymethylpyrrolidine-3-O-[(N,N-diisopropylamino)-2-cyanoethoxyphosphite]

To a solution of N¹-palmitoyl-5-dimethoxytrityloxymethyl -3-hydroxypyrrolidine in CH₂Cl₂ (0.1M) at 0 °C. was added 3 equivalents of diisopropylethylamine, followed by 1.1 equivalents 2-cyanoethyl-N,N-diisopropylaminochlorophosphite. The solution was stirred at 0° C. until all the starting material was consumed. The solvent was removed in vacuo at low temperature and the resulting oil purified by flash chromatography using EtOAc/CH₂Cl₂ containing 1% triethylamine as eluant.

EXAMPLE 17

Synthesis of the 5'-XXXXXXT-3' Phosphate Linked Heptamer 50 milligrams (2 mmole) of 5'-O- dimethoxytritylthymidine bonded to CPG (controlled pore glass) through an ester linkage is taken in a glass reactor, and a dichloromethane solution of 2% dichloroacetic acid (volume/volume) and 5% triethylsilane (volume/volume) is added to deprotect the 5'-hydroxyl groups. The product is washed with acetonitrile. A solution of N¹-palmitoyl-5-dimethoxytrityloxymethylpyrrolidine- 3-O-[(N,N-diisopropyl-amino)- 2-cyanoethoxyphosphite] monomer and a 0.4 M solution of 1H-tetrazole in acetonitrile is then added and allowed to react at room temperature for 2 minutes. The product is washed with acetonitrile and then a solution of iodine (composed of iodine, water, lutidine and tetrahydrofuran) is added and reacted at room temperature for 5 minutes. This oxidation step is repeated one more time for 5 minutes. The support is washed with acetonitrile and then a solution of acetic anhydride/lutidine/THF (1:1:8), and N-methyl imidazole/THF is added to cap any unreacted 5'-hydroxyl groups. The product is washed with acetonitrile. This complete cycle is repeated five more times resulting in the phosphate triester oligomer. Incubation with aqueous ammonia will give the phosphodiester heptamer of XXXXXXT where X represents the phosphate linked oligomer of 5-hydroxymethyl-(N¹-palmitoyl)pyrrolidin-3-yl-penta[   5-phosphatidylmethyl-(N¹-palmitoyl)pyrrolidine-3-yl]-thymidine.

EXAMPLE 18

Synthesis of (5'-TTG-CTT-CCA-TCT-TCC-TCG-TC-3') Phosphorothioate by the Phosphoramidite Method Using Triethylsilane as the Carbocation Scavenger A 46 μmole scale synthesis of (5'-TTG-CTT-CCA-TCT-TCC-TCG-TC- 3';SEQ ID no: 1) phosphorothioate was conducted on a Millipore 8800 Milligen automated synthesizer using the phosphoramidite method using the following protecting groups: the cyanoethoxy group on the phosphorus, the benzoyl group on the exocyclic amine of the deoxycytidine and deoxyadenosine bases, and the isobutyryl group on the exocyclic amine of the deoxyguanosine base. The method was used to carry out two different syntheses. In one synthesis deblocking of the dimethoxytrityl protecting group was carried out using 3% dichloroacetic acid in dichloromethane. In the second synthesis a mixture of 3% dichloroacetic acid and 3% triethylsilane as a carbocation scavenger, in dichloromethane, was used to remove the dimethoxytrityl protecting group. At the completion of the synthesis the oligonucleotides were cleaved from the solid support and the protecting groups were removed using aqueous ammonium hydroxide. The samples were analyzed by polyacrylamide gel electrophoresis and quantified using a densitometer. The yields for the full length oligomers for the control and for the triethylsilane preparations were 76% and 84% respectively.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A process for the synthesis of oligonucleotides comprising the steps of:
 a) attaching a protected nucleoside to a solid support, said nucleoside protected at the 5'-O hydroxyl position with an acid labile protecting group that forms a carbocation upon cleavage with acid;
 b) removing said 5' protecting group with an acidic solution containing a carbocation scavenging agent to give the free 5' hydroxyl;
 c) washing said solid support to remove excess acid solution and scavenged carbocation;
 d) reacting in the presence of a catalyst said free 5' hydroxyl with a nucleotide containing an active phosphite;
 e) oxidizing the phosphite to a phosphate;
 f) capping remaining reactive sites with a solution containing an acid anhydride;
 g) repeating steps b through f at least once for subsequent couplings of additional nucleotides; and
 h) cleaving said oligonucleotide from said solid support.

2. The process of claim 1 wherein step e is performed prior to step f.

3. The process of claim 1 wherein said carbocation scavenging agent is anisole, thioanisole, benzyl mercaptan, ethanediol, pyrrole, and $R_3SiR'$; where $R_3$ is $C^1$–$C_4$-alkyl, phenyl or phenyl mono-substituted by halo, nitro or $C_1$–$C_4$-alkyl; and R' is H or halo.

4. The process of claim 1 wherein the carbocation scavenging agent is present in the acidic solution in the amount of from 1 to 25%.

5. The process of claim 1 wherein the carbocation scavenging agent is present in the acidic solution in the amount of from 1 to 10%.

6. The process of claim 1 wherein the carbocation scavenging agent is present in the acidic solution in the amount of from 4 to 6%.

7. The process of claim 3 wherein said carbocation scavenging agent is triethylsilane.

8. The process of claim 1 wherein said acid labile protecting group is trityl, monomethoxy trityl, dimethoxy trityl, 9-phenylxanthine-9-yl or 9-(p-methoxyphenyl)xanthine-9-yl.

9. A process for the synthesis of oligonucleotides comprising the steps of:
 a) providing a nucleoside that is protected at the 3' hydroxyl position with a base labile protecting group and further protected at the 5' hydroxyl position with an acid labile protecting group that forms a carbocation upon cleavage with acid;
 b) removing said 5' protecting group with an acidic solution, said solution containing a carbocation scavenging agent, to give the free 5' hydroxyl nucleoside;
 c) reacting in the presence of a catalyst said free 5' hydroxyl with a nucleotide containing an active phosphite;
 d) oxidizing the phosphite to a phosphate;
 e) capping remaining reactive sites with a solution containing an acid anhydride;
 f) repeating steps b through e at least once for subsequent couplings to additional nucleotides; and
 g) cleaving the 3' hydroxyl base labile protecting group with a basic solution.

10. The process of claim 9 wherein step d is performed prior to step e.

11. The process of claim 9 wherein said carbocation scavenging agent is anisole, thioanisole, benzyl mercaptan, ethanediol, pyrrole, and $R_3SiR'$; where $R_3$ is $C_1$–$C_4$-alkyl, phenyl or phenyl mono-substituted by halo, nitro or $C_1$–$C_4$-alkyl; and R' is H or halo.

12. The process of claim 9 wherein the carbocation scavenging agent is present in the acidic solution in the amount of from 1 to 25%.

13. The process of claim 9 wherein the carbocation scavenging agent is present in the acidic solution in the amount of from 1 to 25%.

14. The process of claim 9 wherein the carbocation scavenging agent is present in the acidic solution in the amount of from 4 to 6%.

15. The process of claim 11 wherein said carbocation scavenging agent is triethylsilane.

16. The process of claim 9 wherein said acid labile protecting group is trityl, monomethoxy trityl, dimethoxy trityl, 9-phenylxanthine-9-ylor9-(p-methoxyphenyl)xanthine-9-yl.

17. A method for preparing an oligonucleotide, comprising protecting a 5' hydroxyl or 3' hydroxyl group of the ribose or deoxyribose portion of a 5' of 3' terminal nucleoside of said oligonucleotide, with an acid labile protecting group that releases a carbocation when treated with acid, and removing said carbocation by the addition of a carbocation scavenging agent.

18. The method of claim 17 wherein the method for preparing the oligonucleotide is a phosphoramidite, phosphotriester or H-phosphonate process.

19. The method of claim 17 wherein said carbocation scavenging agent is anisole, thioanisole, benzyl mercaptan, ethanediol, pyrrole, and $R_3SiR'$; where $R_3$ is $C_1$–$C_4$-alkyl, phenyl or phenyl mono-substituted by halo, nitro or $C_1$–$C_4$-alkyl; and R' is H or halo.

20. The process of claim 17 wherein the carbocation scavenging agent is present in the acidic solution in the amount of from 1 to 25%.

21. The process of claim 17 wherein the carbocation scavenging agent is present in the acidic solution in the amount of from 1 to 10%.

22. The process of claim 17 wherein the carbocation scavenging agent is present in the acidic solution in the amount of from 4 to 6%.

23. The process of claim 19 wherein said carbocation scavenging agent is triethylsilane.

24. The method of claim 13 wherein said acid labile protecting group is trityl, monomethoxy trityl, dimethoxy trityl, 9-phenylxanthine-9-yl or 9-(p-methoxyphenyl)xanthine-9-yl.

* * * * *

UNITED STATES PATENT AND TRADEMARK OFFICE
CERTIFICATE OF CORRECTION

| | |
|---|---|
| PATENT NO. | : 5,510,476 |
| APPLICATION NO. | : 08/271181 |
| DATED | : April 23, 1996 |
| INVENTOR(S) | : V. Ravikumar et al. |

It is certified that error appears in the above-identified patent and that said Letters Patent is hereby corrected as shown below:

Column 5, line 36, please delete "B" after "$R_3$"

Column 14, line 49, please delete "$d_6$" and insert -- $\underline{d}_6$ -- therefor;

Column 15, line 2, please insert -- , -- after "δ";

Column 15, line 35, please insert a hyphen -- - -- after the "0" in "5'0";

Column 16, line 30, please delete "$ArCHCH_2$" and insert -- $\mathbf{ArCHCH_2}$ -- therefor;

Column 16, line 47, please delete "$_{200}MHz$" and insert -- - 200MHz -- therefor;

Column 17, line 26, please delete "N=" and insert -- $N^1$ -- therefor;

Column 17, line 50, please delete "$COCH_2$" and insert -- $\mathbf{COCH_2}$ -- therefor;

Column 20, line 48, please delete "25%" and insert -- 10% -- therefor;

Signed and Sealed this

Sixth Day of November, 2007

JON W. DUDAS
*Director of the United States Patent and Trademark Office*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1:

```
TTGCTTCCAT CTTCCTCGTC                                   20
```